United States Patent [19]

Tankersley, Jr.

[11] 4,005,224
[45] Jan. 25, 1977

[54] METHOD OF COMBATING INFLUENZA TYPE A AND B AND PARAINFLUENZA TYPE 3 VIRUSES WITH AMINOSPIRANES AND AMINOALKYLSPIRANES

[75] Inventor: Robert Walker Tankersley, Jr., Richmond, Va.

[73] Assignee: A. H. Robins Company, Incorporated, Richmond, Va.

[22] Filed: Apr. 5, 1976

[21] Appl. No.: 674,016

Related U.S. Application Data

[63] Continuation-in-part of Ser. No. 487,950, July 11, 1974, abandoned, which is a continuation-in-part of Ser. No. 350,606, April 12, 1973, abandoned.

[52] U.S. Cl. .................................. 424/325
[51] Int. Cl.² ........................................ A61K 31/13
[58] Field of Search ..................... 424/325
[56] References Cited
UNITED STATES PATENTS 3,214,470 10/1965 Grogan .............................. 424/325

OTHER PUBLICATIONS

The Merck Manual, 12 ed., Merck & Co., Inc., Rahway, N.J., 1972, pp. 16–18.

*Primary Examiner*—Jerome D. Goldberg

[57] ABSTRACT

A method is disclosed for combating influenza utilizing aminospiranes of the formula:

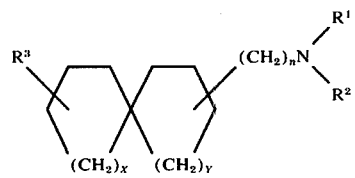

wherein Y is one or two, X is one or two, $n$ is zero to three inclusive, $R^1$ and $R^2$ are hydrogen and lower alkyl, and $R^3$ is hydrogen or methyl.

13 Claims, No Drawings

METHOD OF COMBATING INFLUENZA TYPE A AND B AND PARAINFLUENZA TYPE 3 VIRUSES WITH AMINOSPIRANES AND AMINOALKYLSPIRANES

This application is a continuation-in-part of application Ser. No. 487,950, filed July 11, 1974 now abandoned, which is a continuation-in-part of application Ser. No. 350,606, filed Apr. 12, 1973, now abandoned.

The present invention is concerned with the use of aminospirane compounds to combat viruses and is particularly concerned with a novel method for combating viruses using aminospirane compounds having a primary amino ($-NH_2$) or an aminoalkyl side chain and novel compositions therefor.

The antiviral agents of this invention are illustrated generally by the following formula:

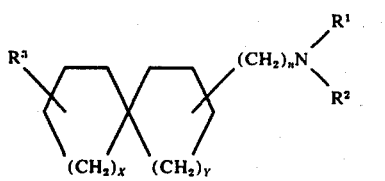

wherein;
$R^1$ and $R^2$ are hydrogen and lower alkyl,
$R^3$ is hydrogen or methyl,
Y is one or two,
X is one or two,
n is zero to three inclusive, and
the pharmaceutically acceptable addition salts thereof.

In the definition of symbols in the foregoing Formula I and where they appear elsewhere throughout this specification, the terms have the following significance.

The term lower-alkyl as used herein includes straight and branched chain radicals of up to six carbon atoms inclusive, preferably no more than four carbon atoms, and is exemplified by such groups as methyl, ethyl, propyl, isopropyl, butyl, sec. butyl, tertiary butyl, amyl, isoamyl, hexyl, and the like.

The invention also includes the pharmaceutically acceptable nontoxic acid addition salts of the bases of Formula I with organic and inorganic acids. Exemplary of such organic salts are those formed with maleic, fumaric, tartaric, succinic acid and the like. Exemplary of such inorganic salts are those formed with hydrochloric, hydrobromic, phosphoric, and sulfuric acids. The preferred salt is the hydrochloride.

It is, therefore, a primary object of the present invention to provide a novel method using aminospiranes for combating viruses which infect living animal bodies.

A further object is to provide a novel method for prophylaxis against viral infections caused by Influenza Type A and B and Parainfluenza Type 3 using aminospiranes.

A still further object is to provide novel compositions containing aminospiranes for prophylaxis against influenza viruses which infect humans.

Additional objects will become apparent to one skilled in the art from the description which follows.

The aminospiranes used in the novel methods and novel compositions of the present invention are known compounds, are disclosed, and methods for their preparation are described in J. Med. Chem. 8, 825–829 (1965), J. Med. Chem. 15, 548–551 (1972) and in U.S. Pat. No. 3,214,470. For a more complete description of the aminospiranes utilizable as antiviral agents within the scope of the present invention and their preparation, the disclosures of the aforementioned journal articles and patent are hereby incorporated by reference as fully as though set forth herein.

The aminospiranes corresponding to Formula I and used in the novel methods and compositions of the present invention are given in Table 1, the melting points referring to their hydrochloride salts. The designation C distinguishes the examples as chemical compounds used in the subsequently disclosed virology examples.

TABLE 1

| Example No. | X | Y | n | $R^1$ | $R^2$ | $R^3$ | Position of $R^1\backslash N-(CH_2)_n-/R^2$ | M.P. °C. |
|---|---|---|---|---|---|---|---|---|
| C-1 | 2 | 1 | 0 | H | H | H | 2 | 258–260 |
| C-2 | 2 | 2 | 0 | H | H | H | 2 | 236–233 |
| C-3 | 2 | 2 | 0 | H | H | H | 3 | 298–300 |
| C-4[a] | 1 | 2 | 0 | H | H | H | 8 | 324–326 |
| C-5 | 2 | 2 | 0 | $CH_3$ | $CH_3$ | H | 2 | 187–188 |
| C-6 | 2 | 2 | 0 | H | $n-C_4H_9$ | H | 3 | 283–284 |
| C-7 | 2 | 2 | 0 | H | H | H | 1 | 289–291 |
| C-8 | 2 | 2 | 1 | $CH_3$ | $CH_3$ | H | 3 | 285–286 |
| C-9 | 2 | 2 | 2 | $C_2H_5$ | $C_2H_5$ | H | 3 | 157–158 |
| C-10 | 2 | 2 | 3 | $CH_3$ | $CH_3$ | H | 3 | 225–226 |
| C-11 | 2 | 2 | 0 | H | H | $CH_3$[a] | 3 | 291–293 |
| C-12 | 1 | 2 | 0 | H | H | H | 7 | 246–247.5 |

[a]The methyl group is in the 9-position.

VIROLOGY

Methods a. Antiviral Test Procedure, Experimental Compounds vs Influenza in the Embryonated Chicken Egg.

The test system consists of 10-day old embryonated chicken eggs, infected via the intra-allantoic route with a dose of either Type A (A2/Taiwan/64) or Type B (B/Lee) influenza adjusted to kill 80–100% of unprotected embryos in 72 hours. Experimental compounds are administered to embryos at dosage of 1 mg. per embryo via the same route either 1 hour prior to or 4 hours after infection.

Controls consist of groups of embryos inoculated with diluent alone and infected with either the challenge inoculum or with a 1:10 dilution of this inoculum. In the case of type A influenza tests, 1-adamantanamine hydrochloride (Aldrich) is administered to one group of embryos at the 0.5 mg. per embryo level which produces 70–100% protection at 72 hours.

Activity is evaluated by comparison of survival of embryos of the various groups at 48 and 72 hours; protection must approximate that of 1-adamantanamine hydrochloride for the experimental compound to be considered as a potential anti-influenza drug.

b. Antiviral Test Procedure, Experimental Compounds vs Parainfluenza in Cell Culture.

The test system consists of monolayers of a continuous human cell line, the HEp-2 cell infected with 30 plaque-forming units of para-influenza type 3 virus and incubated for 48 hours at 35° C.

Experimental compounds are made up in tissue culture medium and applied to the cell cultures immediately after infection, at concentrations of one microgram to 1 mg. per culture. Activity is judged by comparing the number of plaques formed in the control monolayers with the number formed in each treated monolayer and expressing the results in percent plaque reduction. Toxic effects are judged by vital staining of the cell monolayer with neutral red stain. Active compounds are defined as those that show 50% plaque reduction without attendant toxicity at one or more compound concentration levels.

c. Antiviral Test Procedure, Experimental Compounds vs Influenza in the White Mouse.

The test system consists of 10 white mice weighing 20 g. each infected intranasally with a dose of $A_2$/Taiwan strain of Asian influenza virus at a level adjusted to kill 75–100% of the mice in less than 2 weeks. Experimental compounds at various dose levels are administered parenterally at various dosage intervals.

Controls consist of 10 white mice weighing 20 g. each receiving compound vehicle alone by the same route and schedule. In some tests, 1-admantanamine HCL (Aldrich) is administered as a positive control compound.

Activity is evaluated by scoring the day of death of each unprotected animal, scoring surviving animals as total days of test plus 1, and using the "mean survival day" of each group as the indicator of protection. Scores are further evaluated for significance at the 95% confidence limit by the use of Dunnett's $t$ test for comparing treated group survival against control group survival.

d. Antiviral Test Procedure, Experimental Compounds vs Rhinovirus In Cell Culture.

The test system consists of cultures of HeLa cells, a continuous human cell line, infected with Rhinovirus Type 14 in an amount adjusted to destroy all the cells in unprotected cultures within 48 hours when incubated at 35° C.

Experimental compounds are made up in tissue culture medium and applied to the cultures immediately after infection, at concentrations of one microgram to one milligram.

Activity is judged by spectrophotometrically measuring the amount of the vital stain, neutral red, retained by treated cultures and by normal and infected control cultures [Method of Finter, N. B., J. General Virology 5, pp 419–427 (1969)]. Those treated cultures showing dye retention at least 75% of the dye retained by the normal control cultures were judged to have been protected by the compound concentration applied to them. Lower levels of dye retention were considered negative for protection.

Effectiveness of the compositions of this invention in treating influenza is illustrated in the following examples 1 to 4 having the suffix V, which refers to the virological nature of the examples and distinguishes them from the chemical examples. Example V-5 illustrates activity of compounds 8 and 9 against rhinovirus cultures in HeLa cells.

Example V-1 (Influenza A-Chick Embryos)

Protection in terms of survival of chick embryos treated with the subject compounds and challenged with type A influenza virus according to method (a) described above is shown in Table 2.

TABLE 2

| Protection Against Influenza A Viruses In Chick Embryos | | | |
|---|---|---|---|
| Example No. | Chemical Used | Survival 48 hrs. | 72 hrs. |
| C-1 | 2-aminospiro[4.5]decane.HCl | 90% | 70% |
| C-2 | 2-aminospiro[5.5]undecane.HCl | 100% | 100% |
| C-3 | 3-aminospiro[5.5]undecane.HCl | 90% | 80% |
| C-4 | 8-aminospiro[4.5]decane.HCl | 100% | 80% |
| C-5 | 2-dimethylaminospiro[5.5]undecane.HCl | 100% | 100% |
| C-6 | N-butyl-3-aminospiro[5.5]undecane.HCl | 100% | 90% |
| C-7 | 1-aminospiro[5.5]undecane.HCl | 100% | 100% |
|  | adantanamine.HCl | 100% | 80% |
|  | infected control | 100% | 10% |
|  | adantanamine.HCl | 100% | 70% |
|  | infected control | 30% | 10% |
| C-12 | 7-aminospiro[4.5]decane.HCl | 88% | 88% |

Example V-2 (Influenza B-Chick Embryos)

Protection in terms of survival of chick embryos treated with compound of Example 2 according to method (a) above is shown in Table 3.

TABLE 3

| Protection Against Influenza B Virus In Chick Embryos | | | | |
|---|---|---|---|---|
| Ex. No. | Chemical Used | Survival 48 hrs. | 72 hrs. | 96 hrs. |
| C-2 | 2-aminospiro[5.5]undecane.HCl | 100% | 100% | 100% |
|  | Infected control | 100% | 70% | 30% |

Example V-3 (Parainfluenza 3-Human Cell Line)

Antiviral activity in terms of 50% plaque reduction of Parainfluenza 3 virus in HEp-2 monolayers as determined by method (b) above is shown in Table 4.

TABLE 4

Protection Against Parainfluenza 3 Virus in HEp-2 Monolayers

| Example No. | | Active Concentrations micrograms per ml. (non-toxic, 50% plaque reduction) |
|---|---|---|
| C-1 | 2-aminospiro[4.5]decane.HCl | 50 |
| C-3 | 3-aminospiro[5.5]undecane.HCl | 25 micrograms to 1 microgram |
| C-4 | 8-aminospiro[4.5]decane.HCl | 100 |
| C-11 | 3-amino-9-methylspiro[5.5]undecane.HCl | 10 |

Example V-4 (Influenza A-Mice)

Protection in terms of survival of white mice treated with the subject compounds and challenged with $A_2$/Taiwan influenza virus according to method (c) described above is shown in Tables 5 and 6.

TABLE 5

Protection Against $A_2$ Taiwan Influenza Virus In Mice (Single dose prior to infection)[1]

| Example No. | Chemical Used | Mean Survival Day | Dunnett's "t" score* |
|---|---|---|---|
| C-2 | 2-aminospiro[5.5]undecane hydrochloride | 13.00 | 3.39 |
| Positive Control | 1-adamantamine.HCl | 11.2 | 2.48 |
| Control (vehicle alone) | None | 6.3 | — |

[1]Compounds were administered subcutaneously (s.c.) in a single dose of 50 mg/kg (10 mice) before infection; control mice received vehicle dose
*P = at 2.44

TABLE 6

Protection Against $A_2$ Taiwan Influenza Virus In Mice (Multiple Dose)[1]

| Example No. | Chemical Used | Route | Dose, mg/kg | Mean Survival Day | Dunnett's "t" score* |
|---|---|---|---|---|---|
| C-4 | 8 aminospiro[4.5]decane hydrochloride | i.p. | 10.0 | 15.0 | 3.39 |
| C-4 | " | i.p. | 2.5 | 15.0 | 3.39 |
| C-4 | " | s.c. | 10.0 | 9.4 | 0.91 |
| C-4 | " | s.c. | 2.5 | 13.0 | 2.50 |
| Control | (vehicle alone) | s.c. | — | 7.33 | — |

[1]Compound administered by route shown, starting four hours before infection and twice daily for five days thereafter.
*P = 95% at 2.78.

The data set forth in Tables 5 and 6 indicate that the subject compounds display significant antiviral activity against $A_2$/Taiwan influenza virus in white mice.

Example V-5 (Rhinovirus - Cell Culture)

Antiviral activity in terms of compound concentrations allowing 75% of normal stain uptake after infection by Rhinovirus 14 for two compounds as determined by method (d) above are shown in Table 7.

TABLE 7

Activity Against Rhinovirus 14 in Cultures of Hela Cells.

| Example No. | Compound | Active Concentration, Micrograms |
|---|---|---|
| C-8 | 3-dimethylamino-methyl-spiro[5.5]undecane.HCl | 25 |
| C-10 | 3-dimethylamino-propyl-spiro[5.5]undecane.HCl | 5 |

Formulation and Administration

Effective quantities of the agents demonstrated to be effective against influenza viruses may be administered to a living animal body in any one of various ways, for example, orally as in capsules or tablets and parenterally in the form of sterile solutions. The free basic amino compounds, while effective, are preferably formulated and administered in the form of their nontoxic acid addition salts. Fifty to 100 mg. appear optimum per unit dose while usual broader ranges appear to be 25 to 250 mg. per unit dose. Obviously, several unit dosage forms may be administered at the same time.

The formulations which follow are representative for the pharmacologically active compounds of Examples C-1 to C-7 and C-11 and 12 which are active against influenza and which can be used in the form of capsules and injectables for single or multiple dosages.

1. Capsules - Capsules of 25 mg. of active ingredient are prepared. With the higher amounts of active ingredient, reduction may be made in the amount of lactose.

| Typical blend of encapsulation | mg. per capsule |
|---|---|
| Active ingredient, as salt | 25.0 |
| Lactose | 296.7 |
| Starch | 109.0 |
| Magnesium stearate | 4.3 |
| Total | 435.0 |

Uniformly blend the selected active ingredient with lactose and starch and encapsulate the blend.

Additional capsule formulations preferably contain a higher dose of active ingredient and are as follows:

| Ingredients | 50 mg.per capsule | 100 mg.per capsule | 250 mg.per capsule |
|---|---|---|---|
| Active ingredient, as salt | 50.0 | 100.0 | 250.0 |
| Lactose | 271.7 | 231.5 | 126.5 |
| Starch | 109.0 | 99.2 | 54.2 |
| Magnesium stearate | 4.3 | 4.3 | 4.3 |
| Total, mg. | 435.0 | 435.0 | 435.0 |

| (2) Injectable | Per cc |
|---|---|
| Active ingredient, as salt | 100 mg. |
| Preservative, e.g. chlorobutanol | % w/v - 0.5 |
| Water | q.s. to 1 ml. |

What is claimed is:

1. A method for treating viral infections caused by influenza types A and B or parainfluenza type 3 which consists of administering to a living animal body in need of said treatment against said viruses from about 25 milligrams to about 250 milligrams of a compound selected from the group consisting of aminospiranes of the formula:

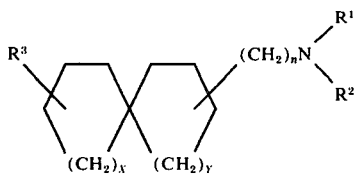

wherein;
Y is one or two,
X is one or two,
n is zero to three inclusive,
$R^1$ and $R^2$ are hydrogen or lower alkyl,
$R^3$ is hydrogen or methyl, and
pharmaceutically acceptable salts thereof.

2. The method in accordance with claim 1 wherein 2-aminospiro[4.5]decane or a pharmaceutically acceptable salt thereof is administered.

3. The method in accordance with claim 1 wherein 2-aminospiro[5.5]undecane or a pharmaceutically acceptable salt thereof is administered.

4. The method in accordance with claim 1 wherein 3-aminospiro[5.5]undecane or a pharmaceutically acceptable salt thereof is administered.

5. The method in accordance with claim 1 wherein 8-aminospiro[4.5]decane or a pharmaceutically acceptable salt thereof is administered.

6. The method in accordance with claim 1 wherein 2-dimethylaminospiro[5.5]undecane or a pharmaceutically acceptable salt thereof is administered.

7. The method in accordance with claim 1 wherein 3-(n-butylamino)spiro[5.5]undecane or a pharmaceutically acceptable salt thereof is administered.

8. The method in accordance with claim 1 wherein 1-aminospiro[5.5]undecane or a pharmaceutically acceptable salt thereof is administered.

9. The method in accordance with claim 1 wherein 3-dimethylaminomethylspiro[5.5]undecane or a pharmaceutically acceptable salt thereof is administered.

10. The method in accordance with claim 1 wherein 3-diethylaminoethylspiro[5.5]undecane or a pharmaceutically acceptable salt thereof is administered.

11. The method in accordance with claim 1 wherein 3-dimethylaminopropylspiro[5.5]undecane or a pharmaceutically acceptable salt thereof is administered.

12. The method in accordance with claim 1 wherein 3-amino-9-methylspiro[5.5]undecane or a pharmaceutically acceptable salt thereof is administered.

13. The method in accordance with claim 1 wherein 7-aminospiro[4.5]decane or a pharmaceutically acceptable salt thereof is administered.

* * * * *